United States Patent [19]
Wakamatsu

[11] Patent Number: 5,659,251
[45] Date of Patent: Aug. 19, 1997

[54] ELECTROMAGNETIC INDUCTIVE PROBE

[75] Inventor: Hideki Wakamatsu, Kobe, Japan

[73] Assignee: Hewlett-Packard Company, Palo Alto, Calif.

[21] Appl. No.: 435,170

[22] Filed: May 5, 1995

[30] Foreign Application Priority Data

Jun. 30, 1994 [JP] Japan .................................. 6-172023

[51] Int. Cl.$^6$ .................................................. G01N 27/07
[52] U.S. Cl. ..................... 324/445; 324/204; 324/225; 336/84 M; 336/84 C
[58] Field of Search ..................... 324/445, 204, 324/225; 336/84 M, 84 C

[56] References Cited

U.S. PATENT DOCUMENTS

| | | | |
|---|---|---|---|
| 3,030,573 | 4/1962 | Yamashita et al. | 324/445 |
| 3,375,511 | 3/1968 | Trimble | 324/642 |
| 3,867,688 | 2/1975 | Koski | 324/445 |
| 4,220,920 | 9/1980 | Gross . | |
| 4,282,487 | 8/1981 | Warren et al. | 324/445 |
| 5,157,332 | 10/1992 | Reese . | |
| 5,268,642 | 12/1993 | Uchidomi | 324/445 |

OTHER PUBLICATIONS

"Measurement Of Humidity And Moisture Content And Monitoring Of Environment" Jpn Soc of Mech. Engr, Gihodo Co. Sep. 25, 1992, pp. 282, 283 (w/translation).

"A Miniature Conductivity Meter"; Australian Journal of Instrumentation & Control., vol. 31, No. 1 Resmar et al.

Primary Examiner—Kenneth A. Wieder
Assistant Examiner—Jose M. Solis

[57] ABSTRACT

A highly accurate electromagnetic-induction-type conductivity and dielectric constant meter is obtained by using a calibration box (instrument) and a structure as below. The conductivity and dielectric constant meter employs an electromagnetic inductive probe which includes a primary transformer composed of a toroidal core with a wound primary coil, a secondary transformer composed of a toroidal core with a wound secondary coil, an electrostatic shield shielding the transformers, and cables that connect the probe to a meter. To eliminate the electrostatic capacity produced by causes other than electromagnetic induction, the structure of the probe is symmetrical. In a first embodiment, the secondary transformer is placed between two parts of the primary transformer, which has two cores of the same shape that are placed symmetrically. The structure, including the primary and secondary transformers, gaps in the electrostatic shields, and cables, are symmetrical with respect to a plane perpendicular to the central axis of the ring shapes and passes through the center of the annular core of the secondary transformer.

7 Claims, 12 Drawing Sheets

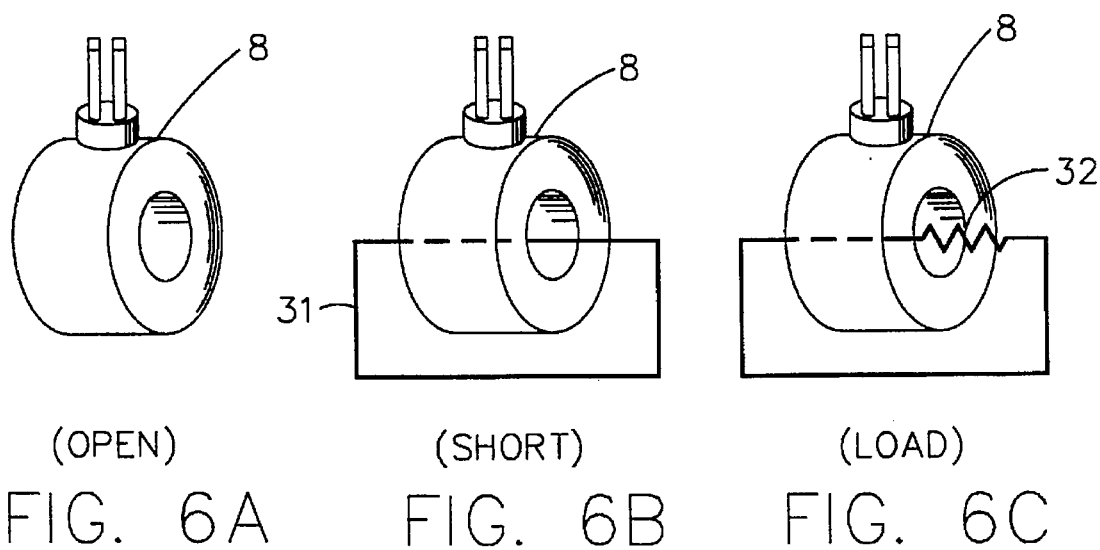
(OPEN) FIG. 6A    (SHORT) FIG. 6B    (LOAD) FIG. 6C
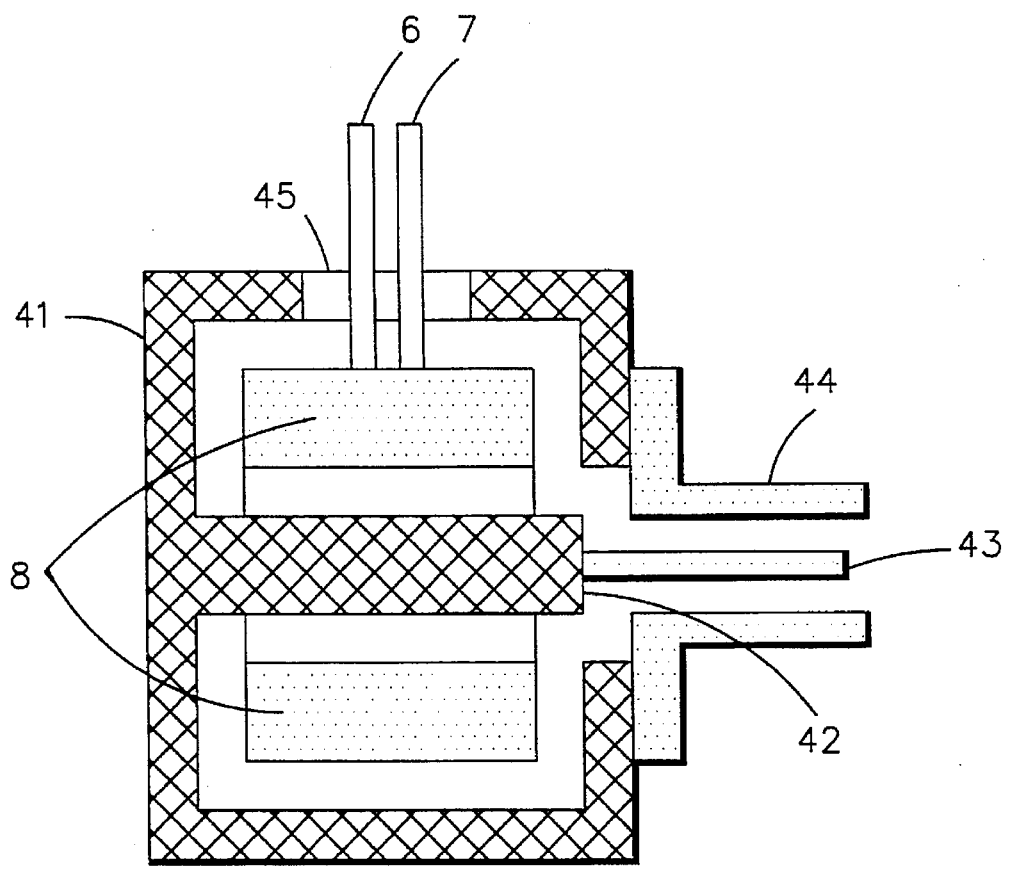
FIG. 7

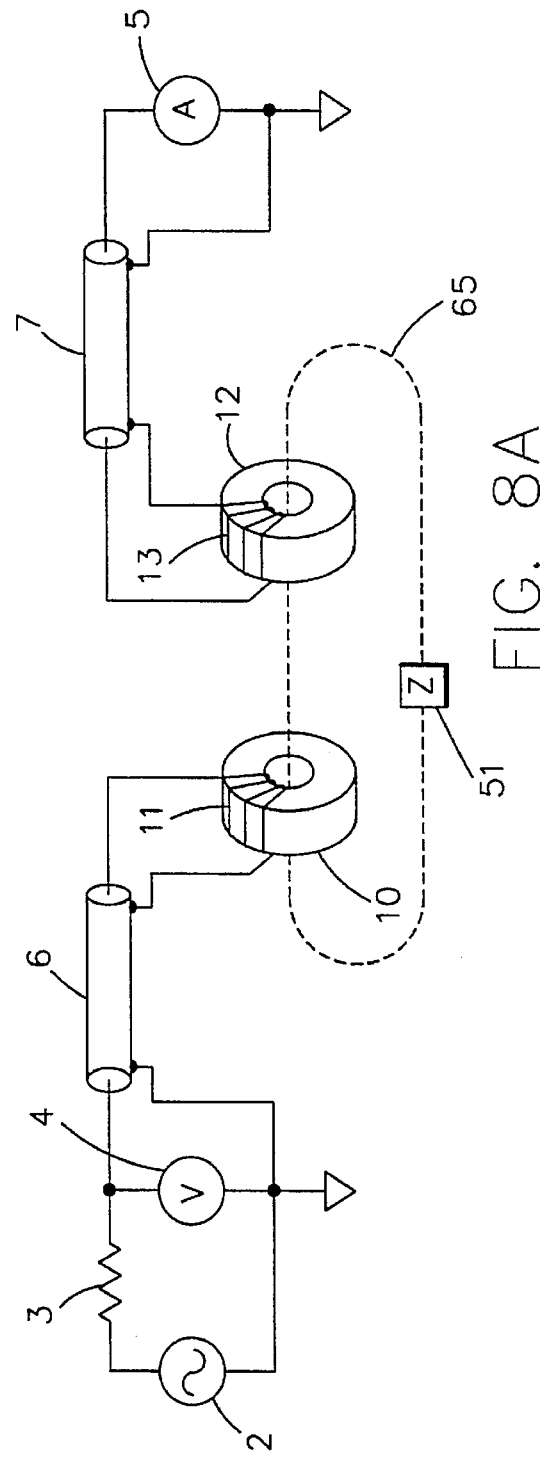
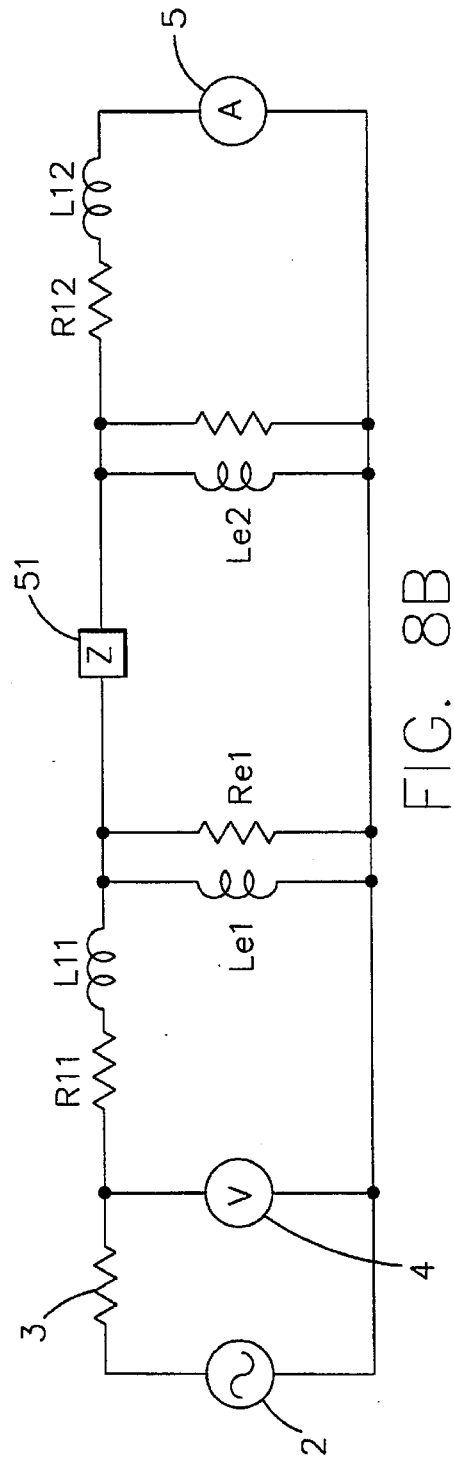
FIG. 8A
FIG. 8B

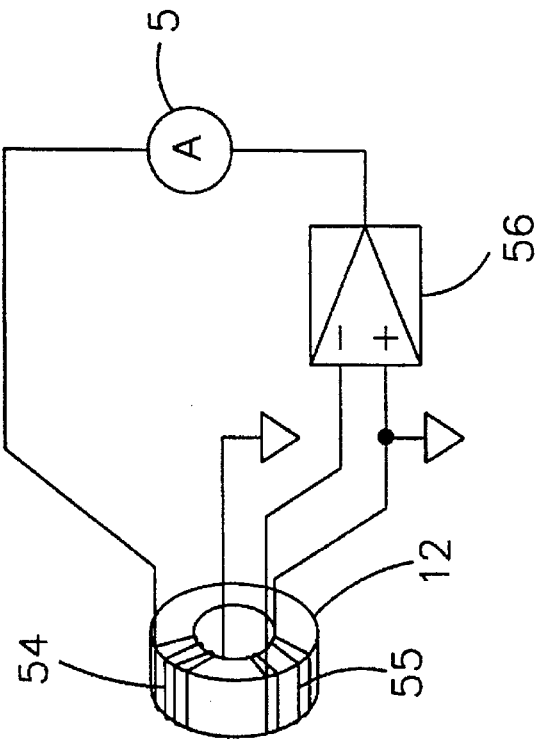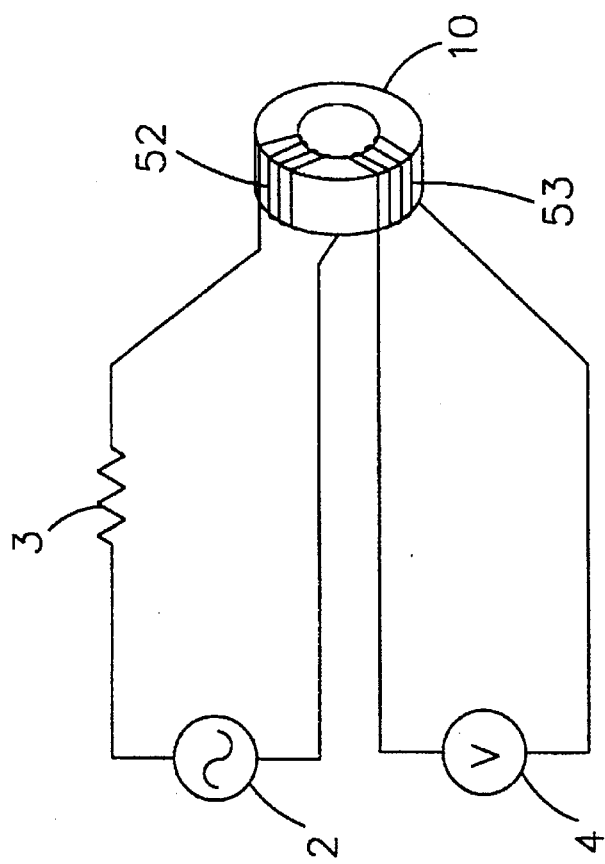
FIG. 9

ELECTROMAGNETIC INDUCTIVE PROBE

FIELD OF THE INVENTION

This invention concerns, in general, impedance measuring devices; and in particular, an electromagnetic inductive probe used in the field of electrical property measurements quantitative research, testing, and control of the structures of colloidal substances, an instrument for correcting the measurements, and a method for making such corrections.

BACKGROUND OF THE ART

Colloids are dispersion systems composed of a particulate-form dispersed substance and a continuous-phase dispersion medium. The dispersed substance and dispersion medium are not uniformly mixed. As a means of evaluating the form of this kind of non-uniform structure, methods are known for measuring its electrical properties, such as conductivity, dielectric constant, etc. In recent years, methods for measuring the dielectric constant by using impedance measurements have been studied. For example, the electrical impedance of food colloids shows somewhat greater electrostatic capacitance than pure water. Means have been developed for detecting the structure of a colloid (dimensions of the particles of the dispersed substance, their density, etc.) from this electrostatic capacity and their frequency properties (frequency distribution).

If an electrostatic capacity measurement, i.e., a dielectric constant measurement, can be practically achieved, a large contribution will have been made to the study of the stabilization of dispersion systems and product quality control.

Even though the advantages of electrostatic capacity measurements are understood, it is difficult in practice to expediently make such measurements. The first reason is that, since (especially with foods) the source is a biological organism, the colloid solutions are aqueous, contain large quantities of ions, have large conductivities and small electrostatic capacities. For example, the magnitude of the susceptance (electrostatic capacitance) in comparison with the conductance of a certain fermentation solution is approximately $1/500$. Nevertheless, the number of fermenting bacteria in the fermentation solution is correlated with its dielectric constant. Therefore, in order to control accurately the fermentation process by measuring electrostatic capacity, which varies with the progress of the fermentation, a resolution of approximately $1/5000$ rad is necessary. The electrostatic capacity measurement values must be correctly separated and isolated so that they are not perturbed by changes in conductance. For this purpose, the phase angle of the complex impedance measurement must be correctly calibrated.

Even though a colloid solution (that is the subject of measurement) is enclosed between 2 electrodes and its electrostatic capacity is measured, such measurement is difficult because a low resistance is equivalently present in parallel with the electrostatic capacity.

The second reason why it is difficult to make electrostatic capacity measurements is a fundamental problem in electrochemistry. Because of the effect of interface polarization of the electrode plates, it is extremely difficult to isolate only the electrostatic capacity of the colloid solution. Interface polarization is primarily an electrostatic capacity effect resulting from a contact impedance produced between the solution and an electrode plate. If this interface polarization could be removed and only the impedance of the solution itself measured, quantitative information concerning the structure of the colloid could be obtained from the measurement's frequency distribution.

When a solution is measured with 2 electrodes, interface polarization is a problem. Since interface polarization is a type of contact impedance, it appears that it can be easily resolved by a 4-terminal measurement (4-terminal method). Such an operation will be discussed in conjunction with FIG. 10 to describe the principle of a 4-terminal measurement. Electrodes 61 and 64 supply current and are immersed in a colloid solution 21 filling a solution tank 20. A signal is applied between electrodes 61 and 64 from signal source 2 and an alternating current is caused to flow into solution 21; the amplitude and phase of the current are measured by ammeter 5. Measurement electrodes 62 and 63 are immersed in solution 21 between electrodes 61 and 64, and the amplitude and phase of the voltage between them is measured by voltmeter 4. It should be possible to obtain the impedance from the ratio of the measured values of voltage and current.

However, even though a theoretical voltmeter with an infinitely large input impedance is used for voltmeter 4, only a small improvement in the interface polarization problem results. The reasons for this are as follows. First, the electrical field produced by the voltage applied between electrodes 61 and 64 must be equipotential on planes parallel to the electrode plates, and potential-measuring electrodes 62 and 63 must be inserted on the respective equipotential planes. It is extremely difficult to practically achieve this arrangement. If they are misaligned, the potentials are different at positions in the longitudinal direction of potential measurement electrodes 62 and 63, and excesses and deficits of current are produced in the electrodes. Moreover, since potential-measuring electrodes 62, 63 have finite thicknesses, part of the solution will be short-circuited, and current excesses and deficits will result. The excesses and deficits of currents passing through the interface between solution 21 and electrodes 61, 64 produce interface polarization. As a result, an interface polarization error is introduced into the calculated impedance value (a ratio of voltage and current).

FIG. 11 is a 4-electrode method that reduces the effect of the interface polarization of FIG. 10. In this figure, the same reference numbers are assigned to the elements which have the same functions as in FIG. 10. The narrow parts of solution tank 20 function like liquid electrodes; they touch the solution columns that are the objects of measurement, without interface polarization. However, as can be predicted, reducing the effects of the interface polarization and trying to measure the solution columns accurately are not necessary compatible. The extension of part of the liquid polarization places strict requirements on the large input impedance, obtained at the voltmeter 4, which is a differential potential difference detector, and requires common mode signal removal. The correction procedure for obtaining high measurement accuracies over a wide frequency range and a wide dielectric constant range becomes complex. In addition, of course, there are inconveniences of operation, such as cleaning.

In order to fundamentally solve the problem of the effects of interface polarization, a measurement technique that requires no electrodes has been proposed, (i.e., eliminating the contact between the electrodes and the solution). In such method, a closed-circuit current is allowed to flow in the solution by electromagnetic induction, and the current is measured by electromagnetic induction. FIG. 12 is a diagram which illustrates the principles of this measurement technique.

A primary transformer, consists of a primary coil 11 wound on a toroidal core 10, and a secondary transformer, consists of a secondary coil 13 wound on a toroidal core 12. When the transformers are immersed in solution 21, the solution completes a circuit therebetween. Therefore, when an alternating current is allowed to flow to primary coil 11 from signal source 2, a closed circuit current 65 is caused to flow in the solution by electromagnetic induction. Due to this closed circuit current 65, an alternating current magnetic flux is produced in toroidal core 12, and an electromagnetic force is produced in secondary coil 13, causing a current to flow. Therefore, if the voltage induced in secondary coil 13 or the current flowing in secondary coil 13 is measured, the closed circuit current is obtained. Since the magnitude of the closed circuit current produced by the electromagnetic induction is proportional to the admittance of solution 21, the dielectric constant can be calculated from the measured value of the closed circuit current. This method does not produce interface polarization, since electrodes are not used as the source of current flowing in the solution.

Therefore, the electromagnetic induction method is primarily a method for measuring solutions with high conductivity; however, it is not a practical method for systems with small dielectric constants, i.e., for the measurement of electrostatic capacities. This is because, when a detection device such as shown in FIG. 12 is used to measure electrostatic capacities, measurement errors are produced by undesired coupling. This undesired coupling is shown in FIG. 13. If there is a coupling between primary coil 11 and secondary coil 13, due to electrostatic capacity 66, a current (other than the closed circuit current due to the original electromagnetic induction) will flow in the secondary coil, introducing an error. Since this electrostatic capacity 66 varies with the solution, it is impossible to compensate for it. Moreover, an error is also produced by the dielectric coupling between the coils due to the stray magnetic flux 67 from the coils. For these reasons, it has not been possible to measure susceptances that are small, in proportion to the conductances of solutions.

OBJECT OF THE INVENTION

The object of this invention is to provide electrical and mechanical structures of the probe part of an electromagnetic-induction-type conductivity and dielectric constant meter which makes possible absolute value determinations of conductivities and dielectric constants with highly accurate linearities.

SUMMARY OF THE INVENTION

This invention makes possible a highly accurate electromagnetic-induction-type conductivity and dielectric constant meter that eliminates the electrostatic capacity produced in a solution transmission pathway from causes other than electromagnetic induction. The invention further improves the resolution of phase angle measurements. A simple, highly accurate calibration device, a geometrical symmetry of structure of the probe and an electrostatic shield between primary and secondary coils are disclosed. The electromagnetic inductive probe has the following structural elements (see FIG. 1): a primary transformer composed of a toroidal core 10 with a primary coil 11 wound on it, a secondary transformer composed of a toroidal core 11 with a secondary coil 13 wound on it, an electrostatic shield 14 shielding the transformers; cables 6 and 7 that connect the probe with main body 1 of the meter, and an outer resin mold 9.

In order to eliminate the electrostatic capacity produced by causes other than electromagnetic induction, the structure of the probe is made symmetrical. In one embodiment of this invention, the secondary transformer is placed between the 2 parts of the primary transformer, which has 2 cores of the same shape that are placed symmetrically. The structure, including the primary and secondary transformers, gaps in the electrostatic shields, and cables, are made symmetrical with respect to a plane perpendicular to the central axis of the ring shapes and passes through the center of the annular core of the secondary transformer.

BRIEF DESCRIPTION OF THE DRAWINGS

FIGS. 3 and 3a shows a third embodiment of this invention;

FIGS. 6a–6c illustrate the principle of employing a 3-point calibration method to the electromagnetic inductive probe;

FIG. 7 shows the basic structure of a calibration instrument incorporating this invention;

FIGS. 8a and 8b show an equivalent circuit of this invention;

FIG. 9 shows how stabilization of core constants is achieved by 2 windings;

EXPLANATION OF SYMBOLS

Figure 1:
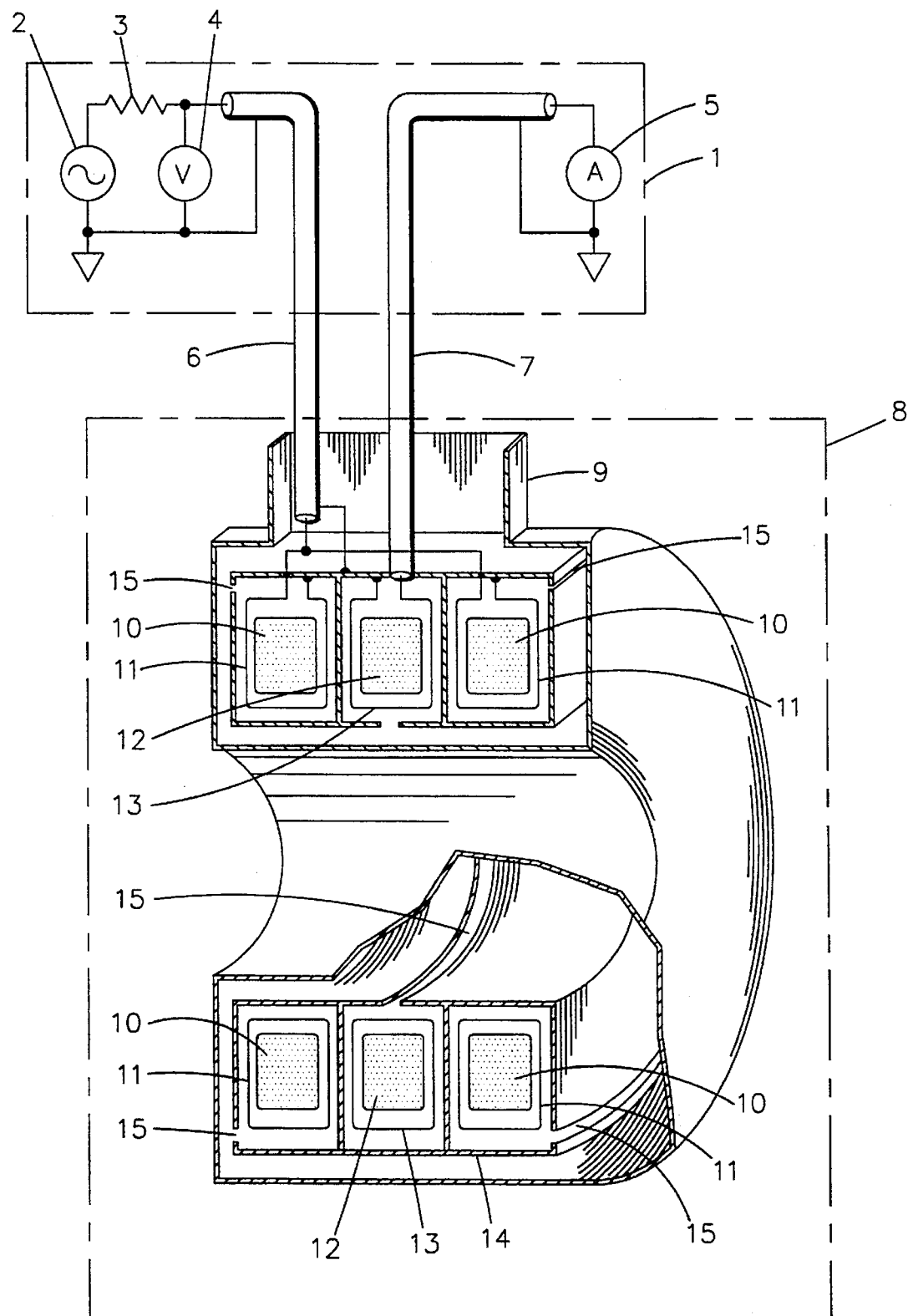
FIG. 1 shows a first embodiment of this invention.

1. Impedance meter
2. Signal source
3. Resistance
4. Voltmeter
5. Ammeter
6. Coaxial cable
7. Coaxial cable
8. Electromagnetic inductive probe
9. Outer resin mold
10. Primary toroidal core
11. Primary coil
12. Secondary toroidal core
13. Secondary coil
14. Shield
15. Gap
16. Hole penetrating through core
17. Short-circuit wire
18. Balun
19. Equivalent circuit of balun
20. Solution tank
21. Colloid solution
22. Offset electrostatic capacity
23. Current circuit producing offset electrostatic capacity 31. SHORT for calibration
32. LOAD resistance for calibration
41. Calibration instrument (main body)
42. Internal projection
43. Inner conductor of coaxial connector
44. Outer conductor of coaxial connector
45. Opening
51. Impedance of colloid solution
52. Primary coil (exciting)
53. Primary coil (for voltage detection)
54. Secondary coil (for current detection)
55. Secondary coil (for detecting magnetic flux)
56. Reverse amplifier
61. Electrode for feeding current
62. Electrode for measuring potential
63. Electrode for measuring potential
64. Electrode for feeding current
65. Closed circuit current produced by electromagnetic induction
66. Parasitic electrostatic capacity
67. Stray magnetic flux Le1, Le2: Exciting inductances L11, L12: Stray inductance and cable inductance Re1, Re2: Exciting resistances R11, R12: Coil resistance and cable conductor resistance

DETAILED DESCRIPTION OF THE INVENTION

Figure 4:
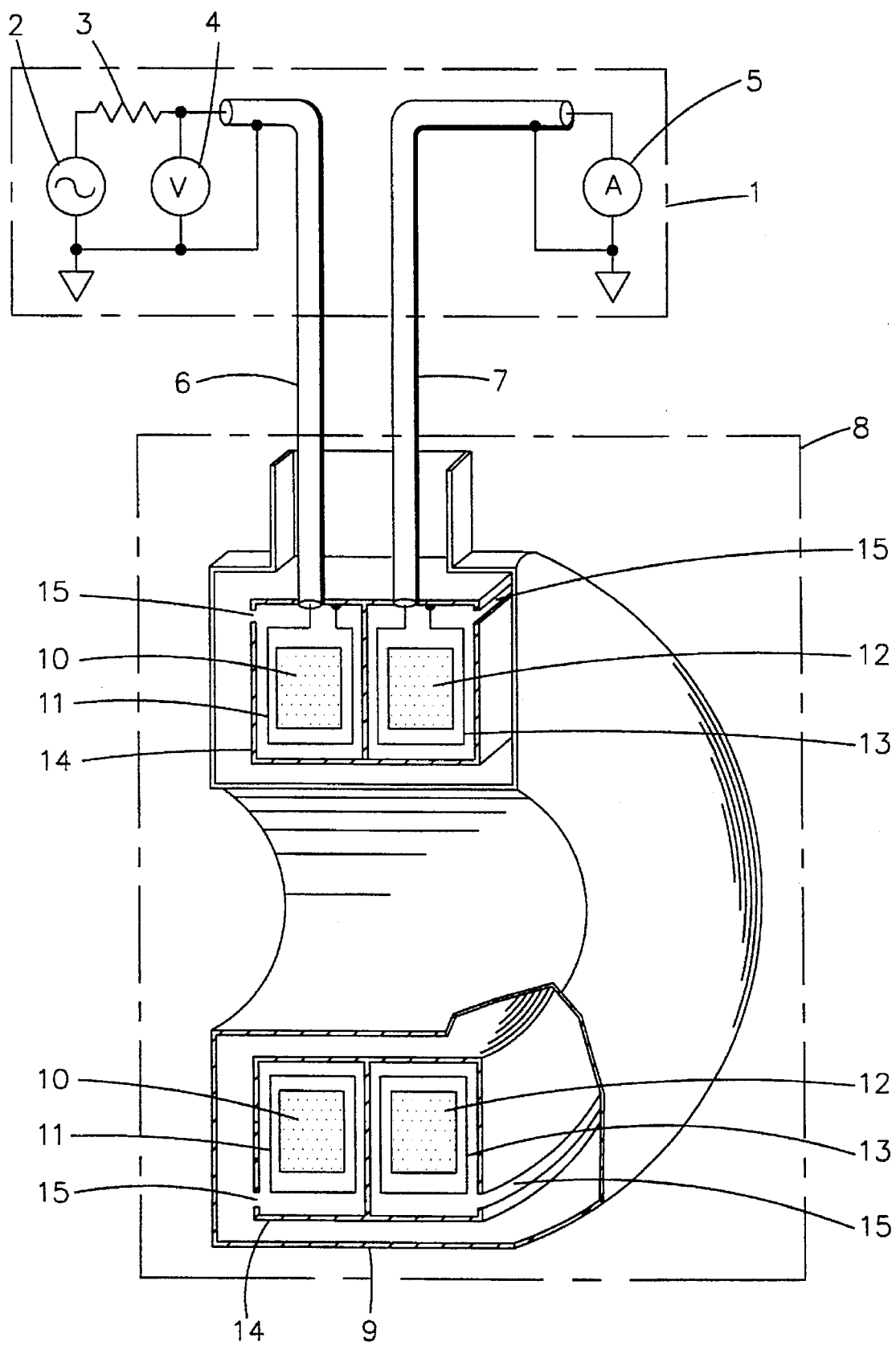
FIG. 4 shows the basic structure of this invention.
Figure 12:
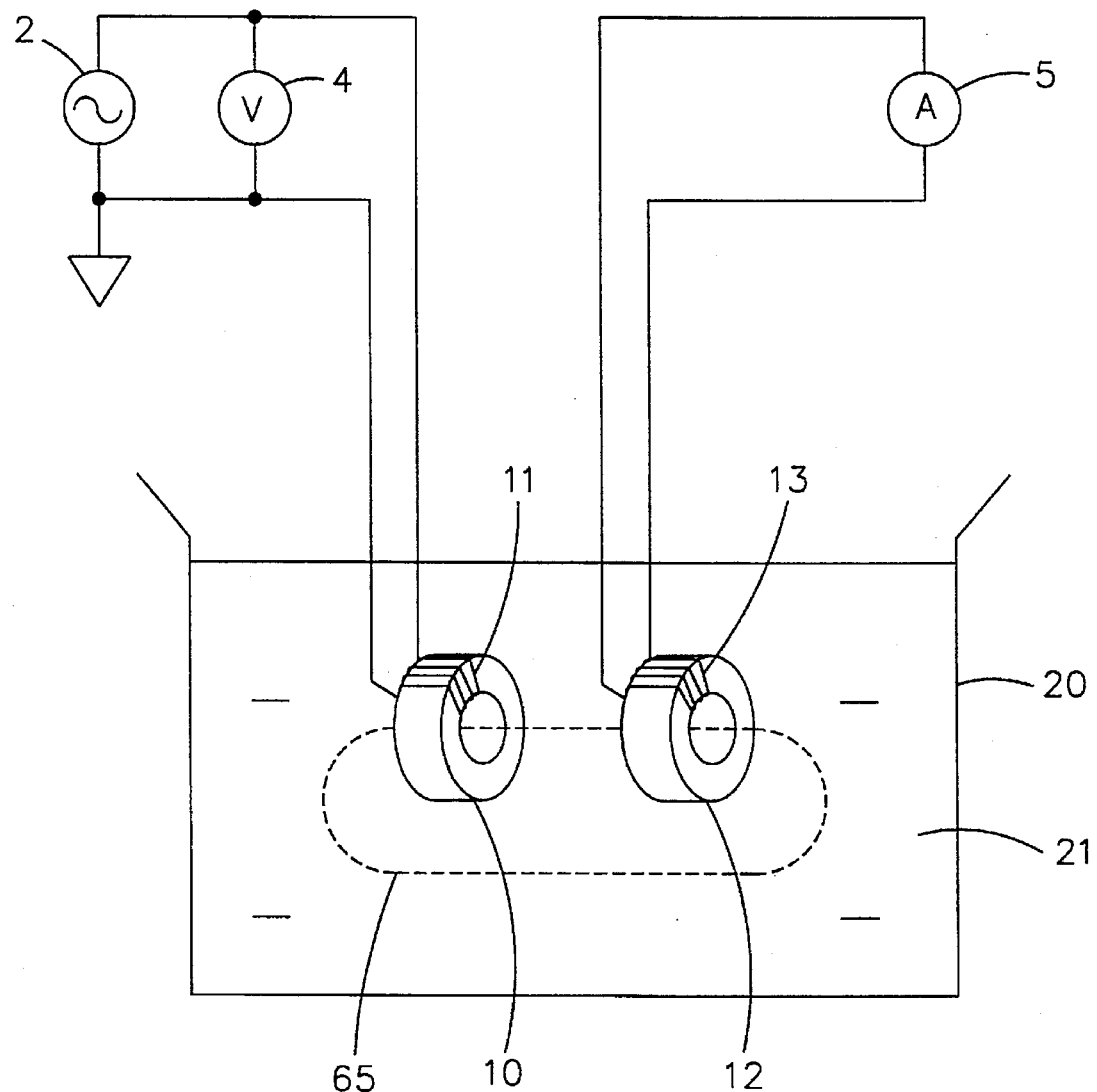
FIG. 12 shows the principle of an electromagnetic-induction-type conductivity meter.
Figure 13:
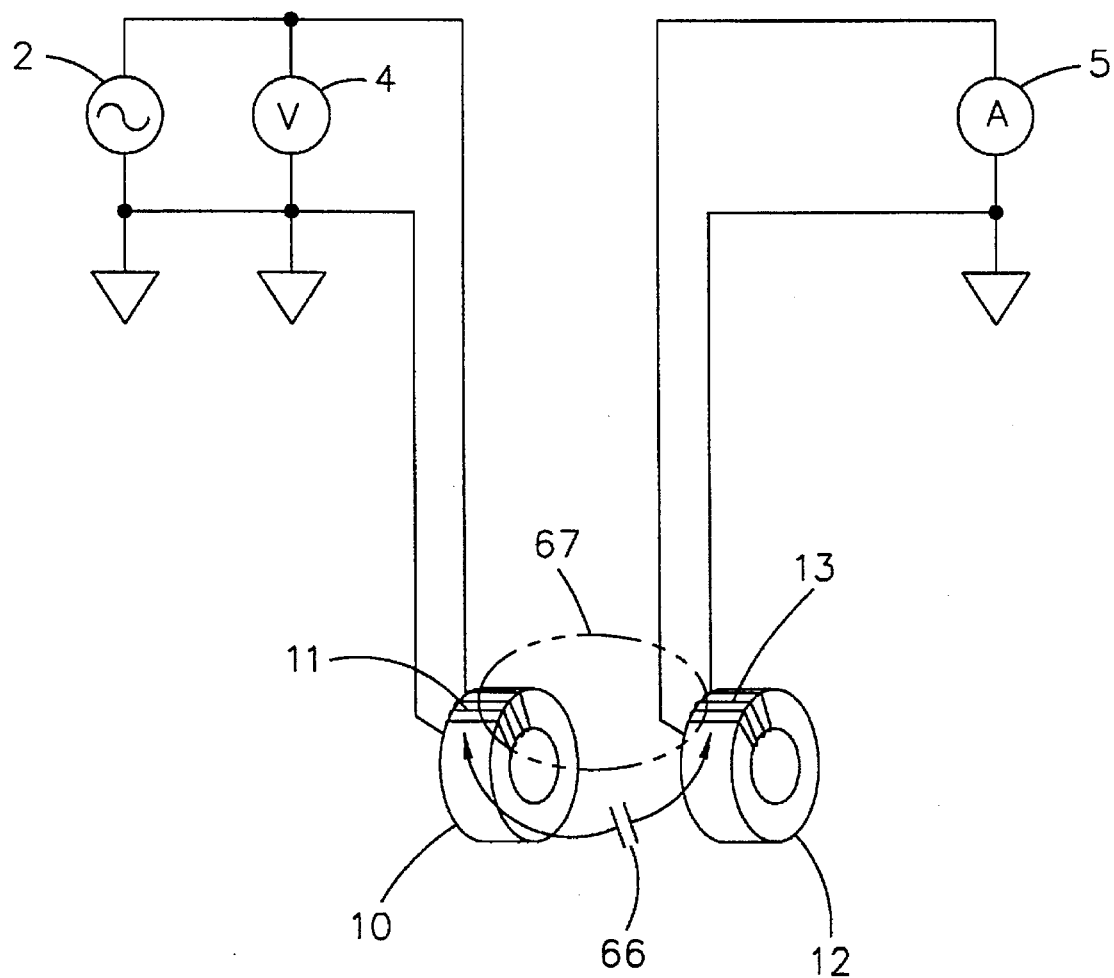
FIG. 13 shows the parasitic coupling which occurs in an electromagnetic-induction-type conductivity meter.

In this invention, problems are solved that arise when an electromagnetic inductive probe is applied to the measurement of electrostatic capacity. First, the parasitic coupling between primary coil 11 and secondary coil 13 (as shown in FIG. 13) is eliminated by means of an electrostatic shield. FIG. 4 shows the basic structure of the probe pan of the invention. FIG. 4 is a perspective view showing a cross section of the electromagnetic inductive probe, cut by a plane passing through the central axis of the toroidal core. The same reference numbers are used in FIG. 4 for the elements with the same functions as in FIG. 12 (this is also the case for the following figures).

An impedance meter 1 is composed of a signal source 2, a resistance 3, a voltmeter 4, and an ammeter 5. Resistance 3 is a current-limiting resistance of the signal source.

Electromagnetic inductive probe 8 includes a primary transformer, formed by a primary coil 11 wound on a toroidal core 10, a secondary transformer, formed by a secondary coil 13 wound on a toroidal core 12, a shield 14, and an outer resin mold 9. Impedance meter 1 and electromagnetic inductive probe 8 are connected by cables 6 and 7. In order to simplify the diagram, the coils are not drawn as though they are wound spirally. Primary coil 11 and secondary coil 13 are separated from each other by shield 14. Shield 14 includes small gaps 15 between it and primary coil 11 and secondary coil 13, so that shorting does not occur.

The structure of FIG. 4 enables parasitic electrostatic capacity to be eliminated. Moreover, the stray magnetic flux is made small, compared to the parasitic electrostatic capacity. At high frequencies, the stray magnetic flux is removed by the shield. Moreover, there arises a microphonic coupling due to magnetic strain oscillations of the core material. In order to prevent this, a suitable buffer material may be placed between the core and outer resin mold 9.

In measuring solutions on a beaker scale, where the solution is not grounded, there is no problem using probes as shown in FIG. 4. However, if the solution container is on a tank scale, and the solution is in a state in which it is close to being grounded, a new problem arises. That problem is the existence of an electrical pathway (of the sort shown in FIG. 5) which causes errors.

Figure 5:
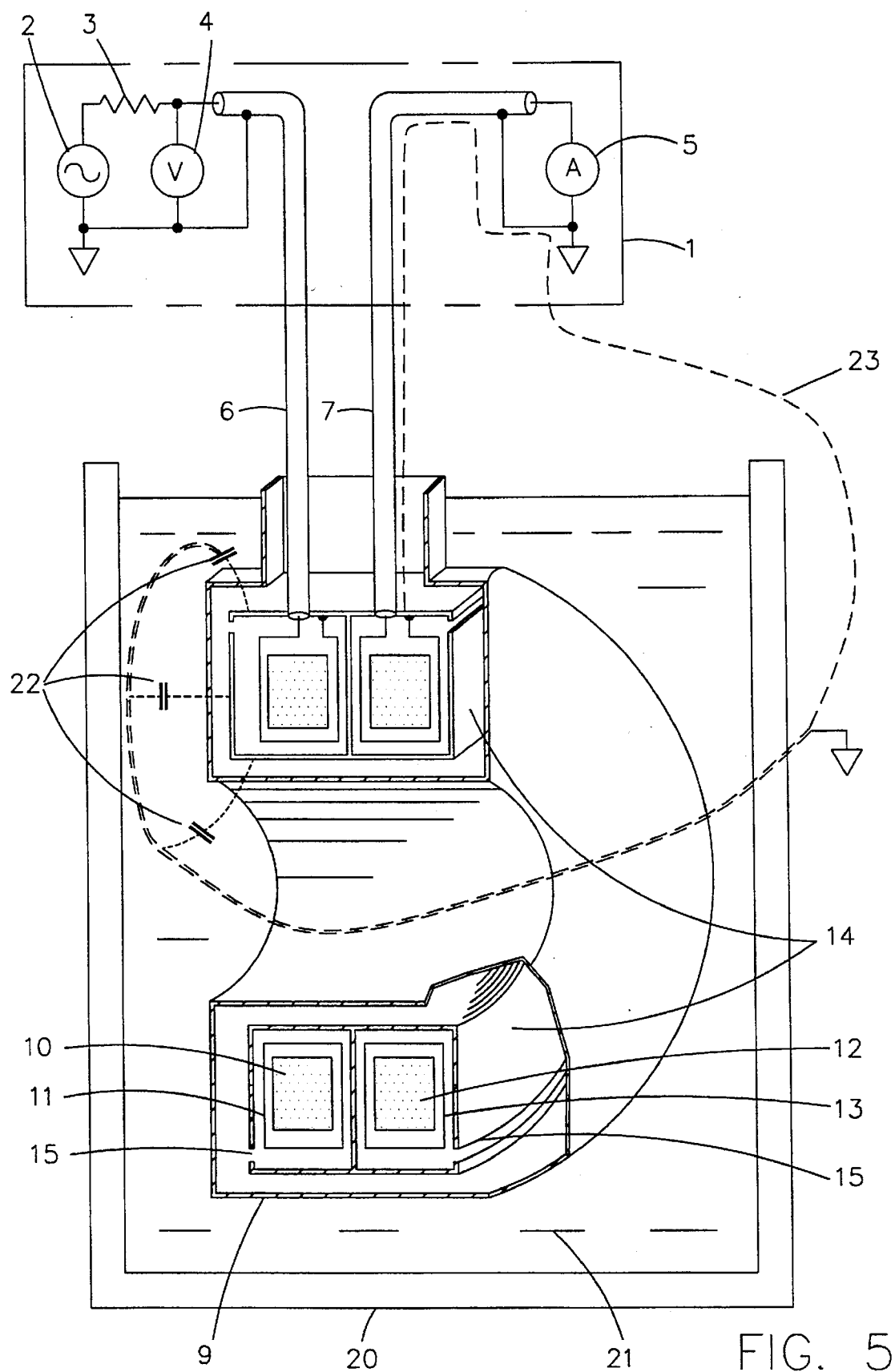
FIG. 5 shows how offset occurs due to the asymmetrical nature of the sense structure.
Figure 10:
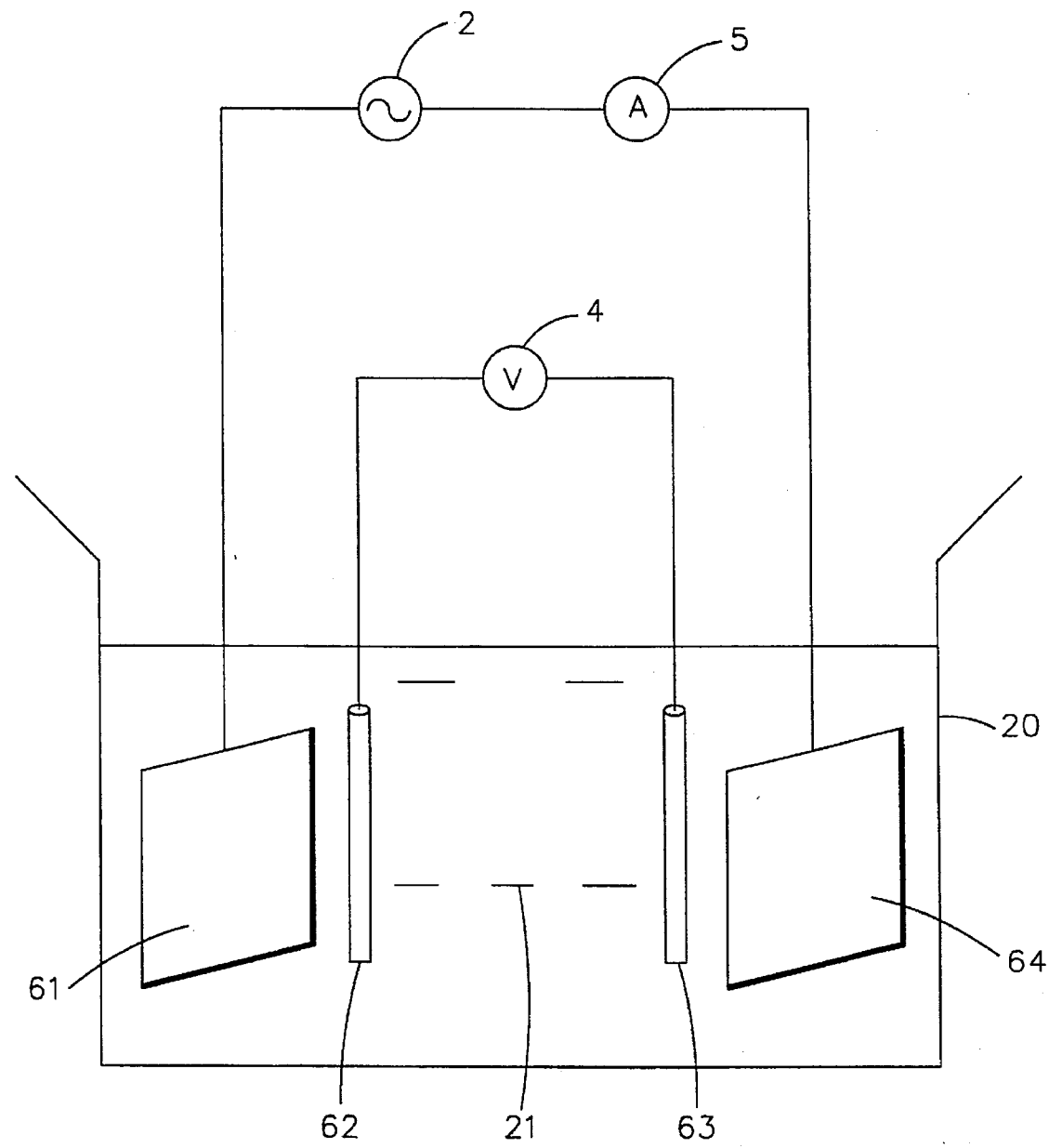
FIG. 10 is a diagram illustrating 4-terminal measurement of a solution.
Figure 11:
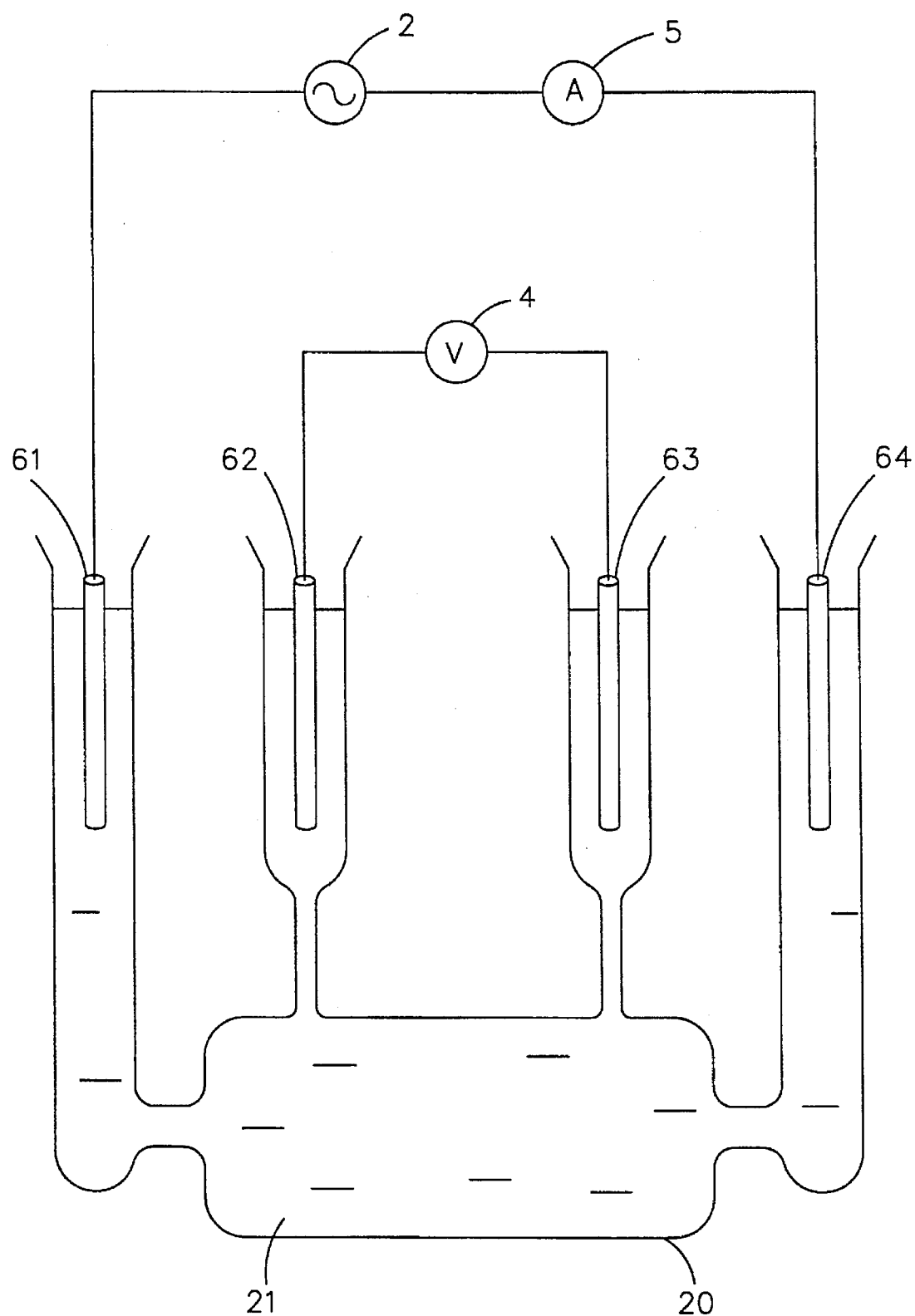
FIG. 11 shows an improved form of a 4-terminal measurement of a solution.

In the probe structure using two coils shown in FIG. 5, the shield structure between the primary and secondary transformers passes through the centers of the ring shapes of the cores of the transformers. It is not symmetrical with respect to a perpendicular plane along the central axis of the rings. Therefore, the primary transformer raises the mean potential of the solution above zero. This is due to the fact that a common mode voltage component is produced with respect to the solution. This is because the potentials distributed at various places on the shield plates, as seen from the current supply point where the outer conductor of cable 6 is connected to the shield 14, and the electrostatic capacity with the solution are not in balance with respect to the aforementioned plane of symmetry.

When the solution is grounded, a current 23 flows to ground due to the aforementioned effect, and if the secondary transformer is asymmetrical on the left and right, a signal is detected which corresponds to the magnitude of this difference. In FIG. 5, the secondary transformer, like the primary transformer, does not have a symmetrical shield structure. The resulting difference is observed as an offset electrostatic capacity 22. Current pathway 23 in FIG. 5 shows the pathway of the imbalance in the asymmetrical current.

It is probably possible to find a current feed position that would not cause this potential difference. However, this invention solves the problem by making the probe structure symmetrical. That is, the structure of the probe is made symmetrical with respect to a plane perpendicular to the central axis of the rings and passing through the center of the core ring of the secondary transformer. Furthermore, for there to be a compensating effect, the symmetrical structure must include the core, the shield structure, and an aperture through which the wiring may be pulled.

Figure 2:
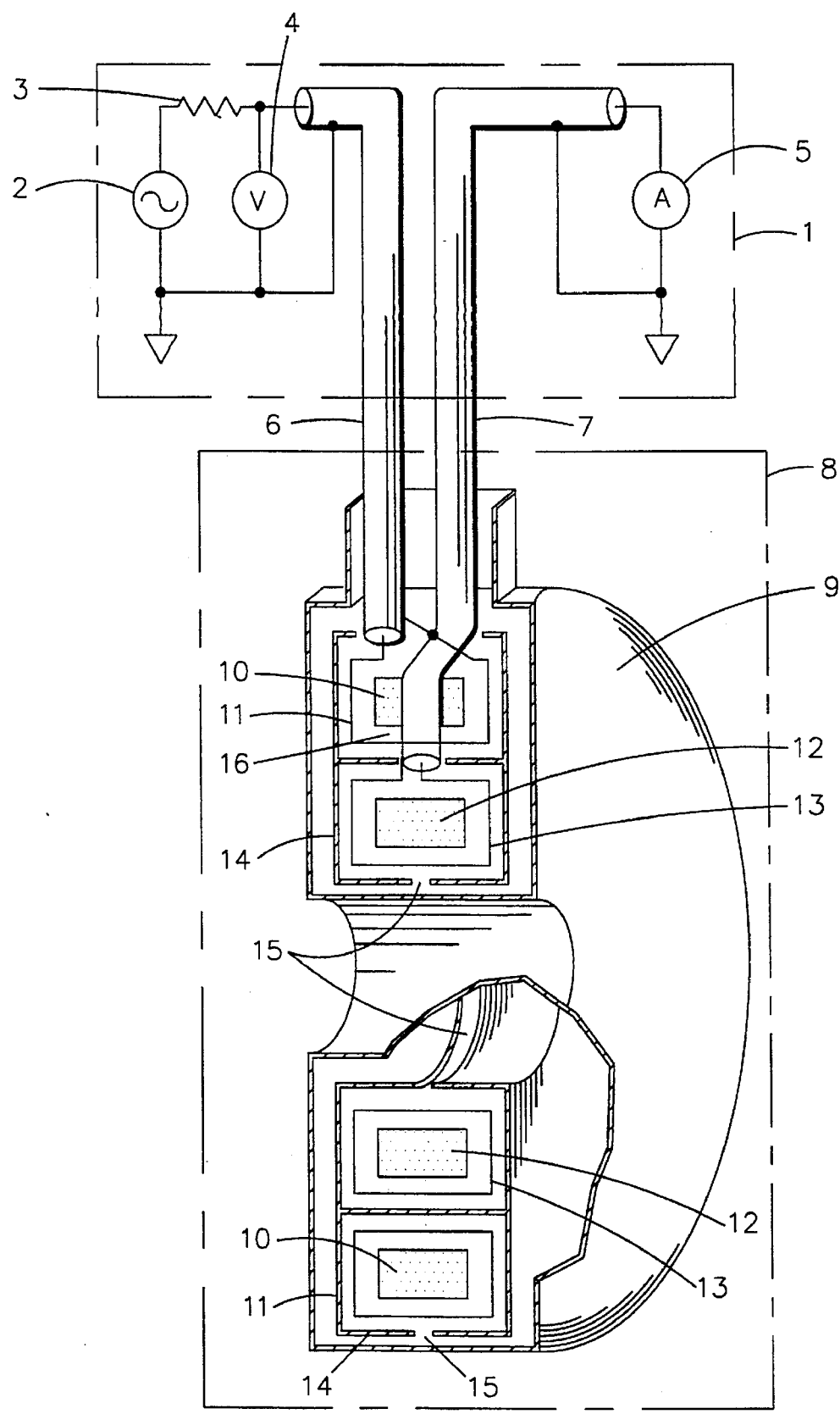
FIG. 2 shows a second embodiment of this invention.

Examples of this embodiment are shown in FIGS. 1, 2, and 3. FIG. 1 is a structure in which the primary transformer is split in two, and the secondary transformer is placed between the 2 parts. In order to produce symmetry with respect to the secondary transformer, the 2 coils of the primary transformer are connected in parallel. The shield gaps are also made symmetrical.

The example of FIG. 2 is a structure in which toroidal cores 10 and 12 have different diameters and are arranged concentrically. For the sake of symmetry, the lead wire from inner coil 13 is passed through a hole 16 in the radial direction, which passes through the center of the cross section of outer core 10 and leads outside the probe.

Figures 3A, 3B:
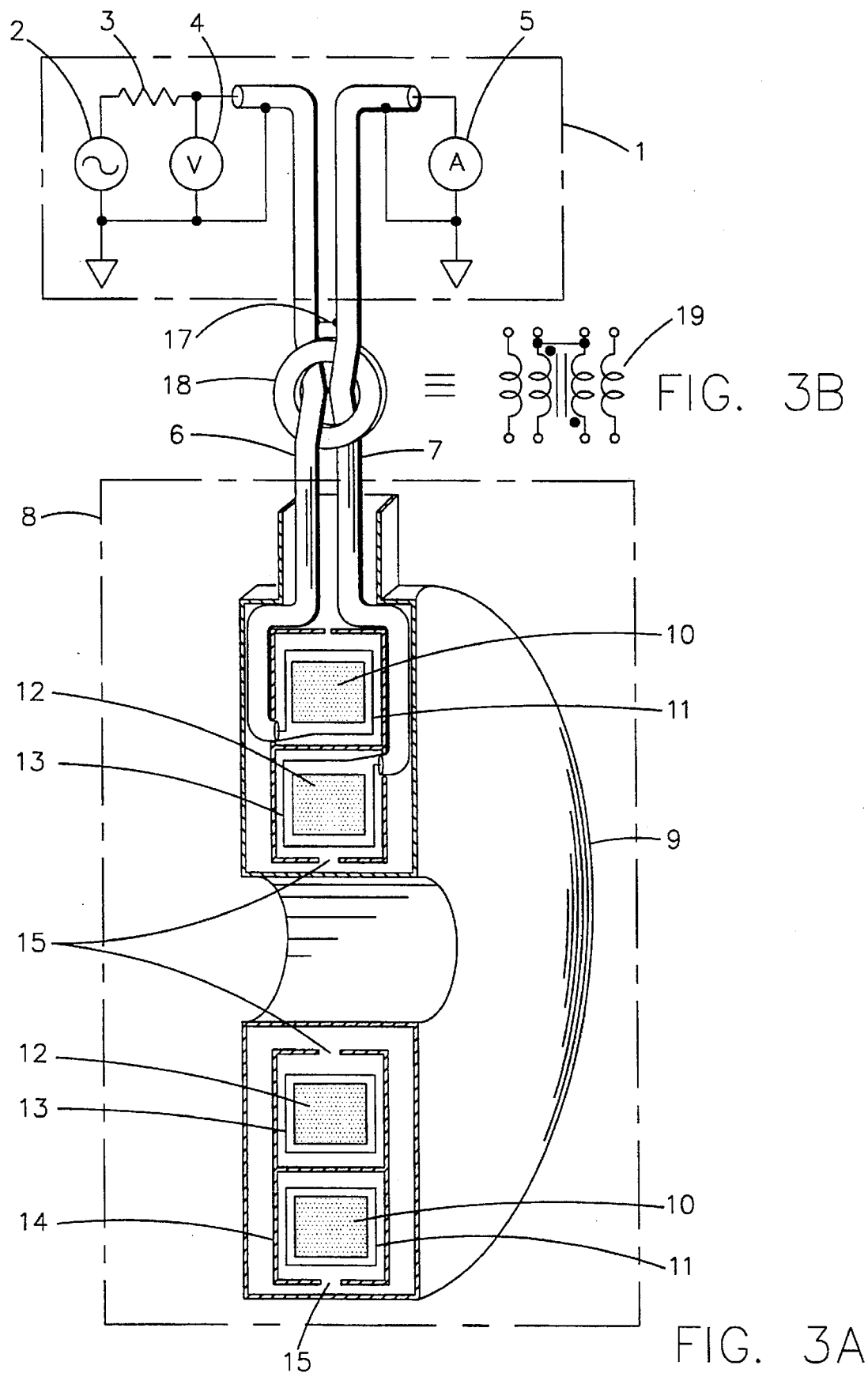

The example of FIG. 3 is a structure in which the cores are arranged concentrically, as in FIG. 2. In this example, the symmetrical structure is destroyed because the lead wires are taken out from the sides of the coils. The potential difference that results is equilibrated and measured by a balun 18. The lead cables 6 and 7 of the primary and secondary transformers are passed through balun 18 from opposite directions and are connected to main meter 1. The outer conductors of the 2 cables are connected to each other by a short-circuiting wire 17, on the measuring device side of the balun. As can be seen from equivalent circuit 19 in FIG. 3a (equivalent to balun 18), cables 6 and 7 are equivalent to transformers wound in opposite directions, and since the outer conductors of the cables have the same potential on the meter side, due to short-circuit wire 17, equilibrium is obtained.

In FIGS. 1, 2, and 3, the same effect can be obtained by structures in which the primary and secondary transformers are exchanged in position.

By the means described above, only the current that is induced by the primary transformer and flows through the solution can be detected by the secondary transformer. However, since the probe of this invention is used by extending it by means of cables 6 and 7 from meter 1, and the probe itself has a residual error that is difficult to calculate, the measurement system as a whole must be calibrated.

It is known that impedance meters are ordinarily calibrated through use of three known impedances. For such a calibration method, see Japan Public Patent Applications Nos. 5-85545 and 5-352215.

It is conceivable that the three known impedances may be obtained by use of prepared solutions, but a simpler, more accurate and more stable calibration method is used by this invention. Since measurement terminals in ordinary impedance meters are used in open, short, and load (i.e., a known resistance) states, it is this concept that is applied to the probe. FIGS. 6a–6c show diagrams of the principle for applying three-point calibration to the electromagnetic inductive probe. For the "OPEN" state, probe 8 is placed in air, for the "SHORT" state, a conductor 31 with 1 winding is passed through probe 8, and for the "LOAD" state, part of the conductor with 1 winding of the SHORT state is replaced with a known resistance 32. Furthermore, in the SHORT state, a current limiting resistor 3 is connected in series with signal generator 2 shown in FIG. 1, etc., so that an over-current does not flow to signal generator 2.

FIG. 7 shows the fundamental structure of an example of a calibration instrument devised to trace the calibration of the measurement system.

In FIG. 7, probe 8 is contained in the calibration instrument. FIG. 7 is a diagram of a cross section through a plane that passes through the central axis of the core of probe 8. The main body 41 of the instrument, made of a conductive material, surrounds the outer surface of probe 8. A projection 42 on the inside of main instrument body 41 passes through the probe and is connected to internal conductor 43 of a coaxial connector. The outside of main instrument body 41 is connected to outer conductor 44 of the coaxial connector. An opening 45 is provided through which pass cables 6 and 7. If probe 8 is enclosed in this structure and a resistor is connected to the coaxial connector, a LOAD state results. If the coaxial connector is short-circuited by a short-circuiting plate, a SHORT state results.

In order to place the probe into this instrument and remove it, a suitable means for dividing and reuniting the main instrument body may be implemented at a suitable position.

Since an instrument incorporating this invention can be connected with a standard by means of the coaxial connector, traceability can be obtained.

Moreover, multipliers for converting from measured impedance values to conductivities and dielectric constants, i.e., the conversion coefficients intrinsic to the probe dimensions, are constant multipliers that need only be obtained once (in the developmental stage of the probe). This is because, if the probe is molded, there are no great variations in its dimensions. Moreover, differences in the dimensions of the probe primarily produce errors in the amplitudes of the measured values, but what is important for measuring minute electrostatic capacities with good accuracy, is the phase accuracy rather than the amplitude accuracy. The phase accuracy is determined by the resistance and inductance component of the LOAD calibration; and it is common knowledge that these can be made extremely stable.

FIGS. 8a and 8b show the basic principle of this embodiment and its equivalent circuit. Impedance 51 that is the subject of measurement can be regarded as a load on closed circuit current 65 (produced by electromagnetic induction in part of the solution). Direct-current resistances (R11 and R12) and stray inductances (L11 and L12) are present in the coils and measurement cables. If the exciting impedance of the cores, i.e., the exciting resistances (Re1 and Re2) and the exciting inductances (Le1 and Le2) vary with temperature, etc., after calibration, differential voltage errors will be produced on the primary side and differential current errors will be produced on the secondary side.

FIG. 9 shows a method for dealing with these effects. As shown in the figure, two primary and two secondary coils are provided. Exciting coil 52 of the primary transformer is connected to signal source 2 through resistance 3. Coil 53 for detecting voltage is connected to voltmeter 4. Current detecting coil 54 of the secondary transformer is connected to one end of ammeter 5 and the ground terminal. The magnetic flux detecting coil 55 is connected to the input of differential amplifier 56, and the output of differential amplifier 56 is connected to the other end of the ammeter 5. By means of this structure, a voltage proportional to the net magnetic flux of core 10 is detected by voltmeter 4. Moreover, since feedback is applied so that the magnetic flux of core 12 of the secondary transformer becomes zero, all of the current flows to ammeter 5. Therefore, stability with respect to temperature changes, etc., is achieved.

This method can, of course, be applied to the examples shown in FIGS. 1, 2, and 3. Furthermore, resistance 3, besides limiting the current in the SHORT state of the calibration so that an over-current does not flow to signal generator 2, also serves as a current limiter. When the measured impedance in the circuit of FIG. 9 is small. This prevents the instrument from becoming unstable at such times.

Examples of this invention have been shown above, but it is not limited to the lay-outs, part forms, arrangements, etc., of the examples, and, if desired, modifications of the structure may be performed, as long as the essential elements of this invention are not lost.

Moreover, this invention is not only effective in measuring liquids, but also in so-called "clamp"-type impedance meters for measuring circuits without cutting them.

EFFECTIVENESS OF INVENTION

By means of this invention, it is possible to measure very small electrostatic capacities of colloidal solutions. The invention solves the problem of interface polarization, and allows the resistance component to be measured with high accuracy.

What is claimed is:

1. An electromagnetic inductive probe, comprising:
   an annular primary transformer and an annular secondary transformer, both transformers positioned so that central axes of cores of said annular primary transformer and said annular secondary transformer are coincident and wherein centers of both of said cores of said annular primary transformer and said annular secondary transformer are coincident; and electrostatic shield means positioned thereabout and including gaps which prevent a short circuiting of the primary and secondary transformers.

2. An electromagnetic inductive probe in accordance with claim 1, wherein said annular primary transformer and said annular secondary transformer have internal structures that are symmetrical with respect to a plane that is perpendicular to said central axes and passes through said centers of both of said cores.

3. An electromagnetic inductive probe in accordance with claim 2, wherein said annular primary transformer surrounds said annular secondary transformer.

4. An electromagnetic inductive probe in accordance with claim 3, further comprising:

lead wires connected to the annular secondary transformer, said lead wires passing radially through a center of a cross section of a core of said annular primary transformer.

5. An electromagnetic inductive probe in accordance with claim 3, further comprising:

an input lead wire connected to said annular primary transformer, an output lead wire connected to said annular secondary transformer, said input lead wire and output lead wire respectively positioned on opposite sides of a plane perpendicular to said central axes and passing through said coincident centers, and a balun, said input lead wire and output lead wire passing through an aperture in said balun and from opposite sides of said balun and connecting to a meter, said input lead wire and output lead wire having shield conductors connected on a meter side of the balun in a short circuit.

6. An electromagnetic inductive probe, comprising:

an annular primary transformer and an annular secondary transformer, both transformers positioned so that central axes of cores of said annular primary transformer and said annular secondary transformer are coincident, said annular primary transformer and annular secondary transformer having internal structures that are symmetrical with respect to a plane that is perpendicular to said central axes; and electrostatic shield means completely surrounding and isolating said annular primary transformer from said annular secondary transformer, said electrostatic shield means including gaps that are disposed on opposed surfaces of said electrostatic shield means and prevent a short circuiting of the primary and secondary transformers;

an input lead wire connected to said annular primary transformer, and an output lead wire connected to said annular secondary transformer, said input lead wire and output lead wire respectively positioned on opposite sides of a plane perpendicular to said central axes.

7. An electromagnetic inductive probe, comprising:

an annular primary transformer including two cores having a same shape and positioned about an plane of symmetry in a parallel and mirror-symmetrical manner and an annular secondary transformer symmetrically positioned between said two cores, both transformers positioned so that central axes of cores of said annular primary transformer and said annular secondary transformer are coincident, said annular primary transformer and annular secondary transformer having internal structures that are symmetrical with respect to said plane of symmetry, said plane of symmetry perpendicular to said central axes;

electrostatic shield means surrounding and isolating said annular primary transformer from said annular secondary transformer;

an input coaxial conductor connected to said annular primary transformer, and an output coaxial conductor, including a shield conductor, connected to said annular secondary transformer, said shield conductor connected to said electrostatic shield means at a point coincident with said plane of symmetry.

* * * * *